United States Patent [19]
Belleau et al.

[11] Patent Number: 5,047,407
[45] Date of Patent: Sep. 10, 1991

[54] 2-SUBSTITUTED-5-SUBSTITUTED-1,3-OXA-THIOLANES WITH ANTIVIRAL PROPERTIES

[75] Inventors: Bernard Belleau, Westmount; Nghe Nguyen-Ba, Brossard, both of Canada

[73] Assignee: IAF BioChem International, Inc., Montreal, Canada

[21] Appl. No.: 308,101

[22] Filed: Feb. 8, 1989

[51] Int. Cl.⁵ ................ A61K 31/505; C07D 411/04
[52] U.S. Cl. ................................. 514/274; 514/262; 514/266; 544/212; 544/276; 544/277; 544/313; 544/314; 544/317
[58] Field of Search ................ 544/313, 314, 317; 514/274

[56] References Cited

U.S. PATENT DOCUMENTS

| | | | |
|---|---|---|---|
| 4,000,137 | 12/1976 | Dvonch et al. | 544/317 X |
| 4,336,381 | 6/1982 | Nagata et al. | 544/313 |
| 4,415,573 | 11/1983 | Ochi et al. | 544/313 X |

FOREIGN PATENT DOCUMENTS

| | | | |
|---|---|---|---|
| 0059171 | 5/1977 | Japan | 544/313 |
| 0021178 | 2/1978 | Japan | 544/313 |
| 0167685 | 12/1981 | Japan | 544/313 |
| 0169689 | 12/1981 | Japan | 544/313 |
| 1035023 | 8/1983 | U.S.S.R. | 544/314 |

OTHER PUBLICATIONS

Mitsuya et al., "3'-Azido-3'-Deoxythmidine (BW A509U): An Antiviral Agent that Inhibits the Infectivity and Cytophatic Effect of Human T-Lymphotropic Virus Type III/Lymphadenopathy-Associated Virus In Vitro", *Proc. Natl. Acad. Sci. USA*, 82, pp. 7096-7100 (1986).
Mitsuya et al., "Inhibition of the In Vitro Infectivity and Cytophatic Effect of Human T-Lymphotropic Virus Type III/Lymphadenopathy-Associated Virus (HTLV-III/LAV) BY 2',3'-Dideoxynucleosides", *Proc. Natl. Acad. Sci. USA*, 83, pp. 1911-1915 (1986).
Balzarini et al., "Potent and Selective Anti-HTLV-III/LAV Activity of 2',3'-Dideoxycytidinene, The 2',3'-Unsaturated Derivative of 2',3'-Dideoxycytidine", *Biochemical and Biophysical Research Communications*, 140(2), pp. 735-742 (1986).
Baba et al., "Both 2',3'-Dideoxythymidine and Its 2',3'-Unsaturated Derivative (2',3'-Dideoxythymidinene) Are Potent and Selective Inhibitors of Human Immunoefficiency Virus Replication In Vitro", *Biochemical and Biophysicals Research Communications*, 142(1), pp. 128-134 (1987).
Lin et al., "Synthesis and Antiviral Activity of Various 3'-Azido, 3'-Amino 2',3'-Unsaturated and 2',3'-Dideoxy Analogues of Pyrimidine Deoxyribonucleosides Against Retroviruses", *J. Med. Chem.*, 30, pp. 440-444 (1987).
Herdewijn et al., "3'-Substituted 2',3'-Dideoxynucleoside Analogues as Potential Anti-HIV (HTLV-III/LAV) Agents", *J. Med. Chem.*, 30, pp. 1270-1278 (1987).
Hallonquist et al., "Studies on Reactions Relating to Carbohydrates and Polysaccharides", *Canadian Journal of Research*, 7, pp. 129-136 (1933).

*Primary Examiner*—Diana G. Rivers
*Attorney, Agent, or Firm*—James F. Haley, Jr.; Leslie A. McDonell

[57] ABSTRACT

Methods and compositions for preventing or treating human immunodeficiency virus (HIV) infections characterized by 2-substituted-5-substituted-1,3-oxathiolanes.

13 Claims, 1 Drawing Sheet

SCHEME 1
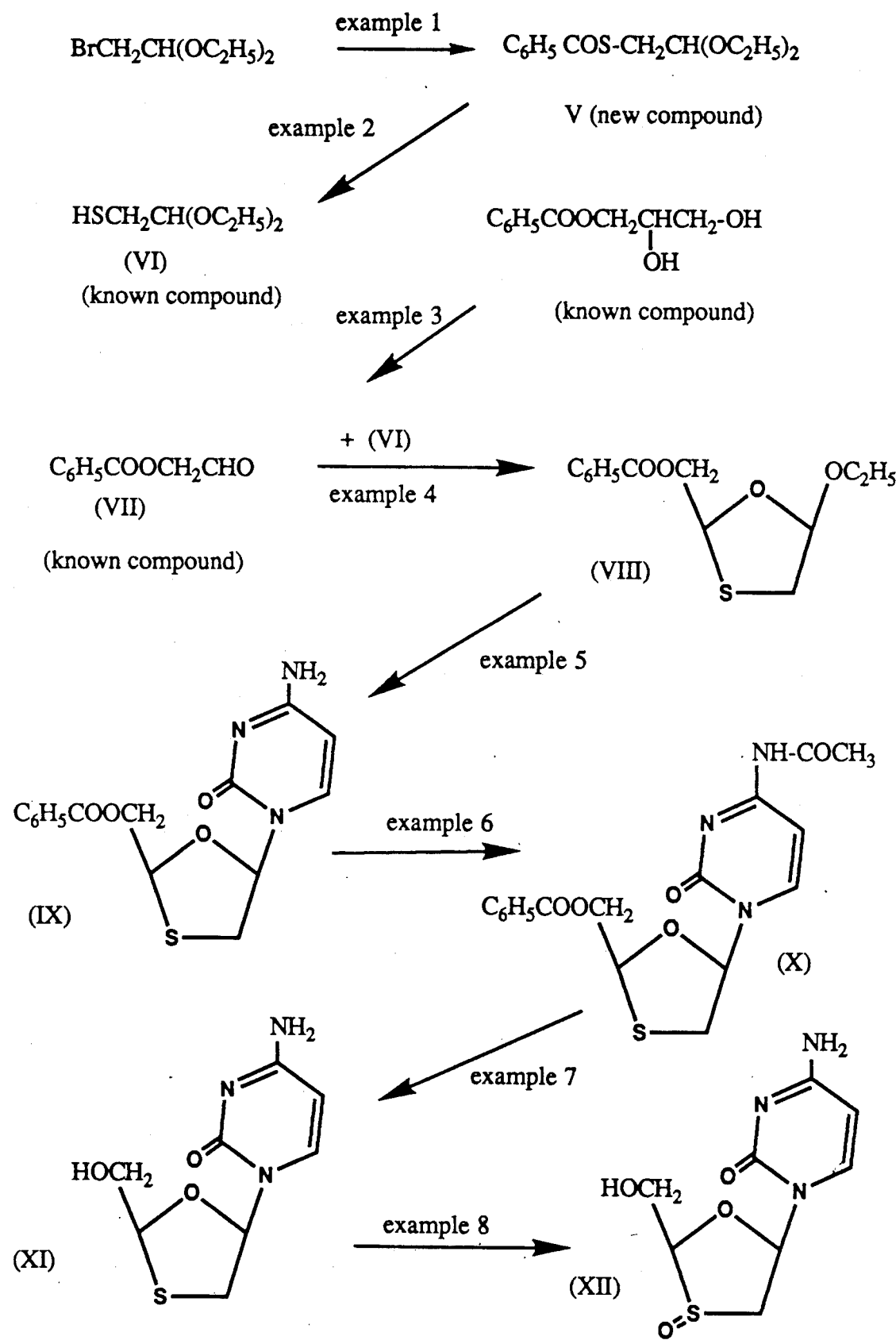

2-SUBSTITUTED-5-SUBSTITUTED-1,3-OXATHIOLANES WITH ANTIVIRAL PROPERTIES

TECHNICAL FIELD OF INVENTION

The present invention relates to novel substituted 1,3-oxathiolane cyclic compounds having pharmacological activity, to processes for and intermediates of use in their preparation, to pharmaceutical compositions containing them, and to the use of these compounds in the antiviral treatment of mammals.

BACKGROUND ART

Retroviral infections are a serious cause of disease, most notably, the acquired immunodeficiency syndrome (AIDS). The human immunodeficiency virus (HIV) has been recognized as the etiologic agent of AIDS and compounds having an inhibitory effect against HIV multiplication have been actively sought.

Mitsuya et al., "3'-Azido-3'-deoxythymidine (BW A509U): An antiviral agent that inhibits the infectivity and cytopathic effect of human T-lymphotropic virus type III/lymphadenopathy-associated virus in vitro", Proc. Natl. Acad. Sci. U.S.A., 82, pp. 7096–7100 (1985), refers to a compound of formula (A) (3'-azido-2'3'-dideoxythymidine), commonly referred to as AZT. This compound is said to be useful in providing some protection for AIDS carriers against the cytopathogenic effect of immunodeficiency virus (HIV).

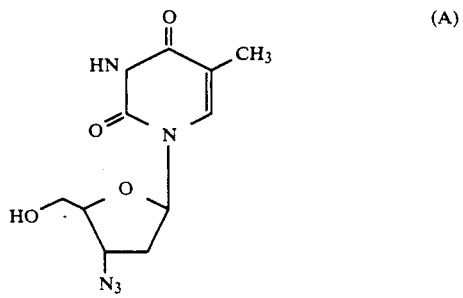

(A)

Mitsuya et al., "Inhibition of the in vitro infectivity and cytopathic effect of human T-lymphotrophic virus type III/lymphadenopathy-associated virus (HTLV-III/LAV) by 2'3'-dideoxynucleosides", Proc. Natl. Acad. Sci. U.S.A., 86, pp. 1911–15 (1986), have also referred to a group of 2',3'- dideoxynucleosides shown in Formula (B) which are said to possess protective activity against HIV-induced cytopathogenicity.

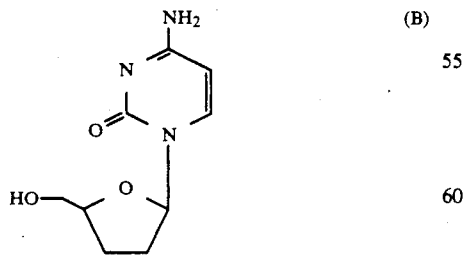

(B)

Balzarini et al., "Patent and selective anti-HTLV-III/LAV activity of 2',3'-dideoxycytidinene, the 2',3'-unsaturated derivative of 2',3'-dideoxycytidine", Biochem. Biophys. Res. Comm., 140, pp. 735–42 (1986), refer to an unsaturated analogue of these nucleosides—2'3'-dideoxy-cytidine, shown in Formula (C)—as being characterized by antiretroviral activity.

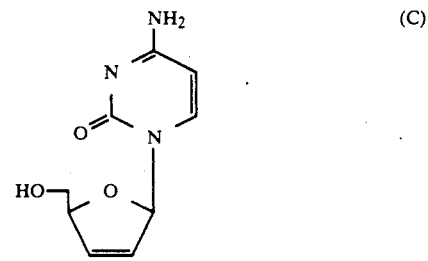

(C)

Baba et al., "Both 2',3'-dideoxythimidine and its 2',3'-unsaturated derivative (2',3'-dideoxythymidinene) are potent and selective inhibitors of human immunodeficiency virus replication in vitro", Biochem. Biophys. Res. Comm., 142, pp. 128–34 (1987), refer to the 2',3'-unsaturated analogue shown in Formula (D) of 2',3'-dideoxythymidine. This analogue is purported to be a potent selective inhibitor of HIV replication.

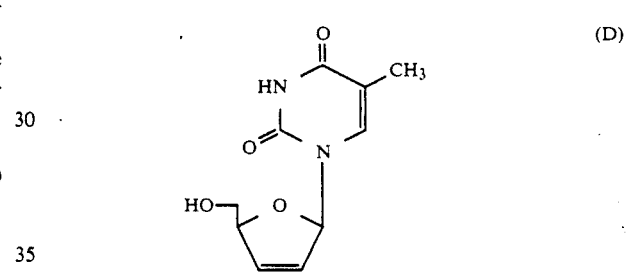

(D)

Analogues of AZT known as 3'-azido-Z', 3'-dideoxyuridine shown in Formula (E), where bromine or iodine have been said to have an inhibitory activity against Moloney murine leukemia in T. S. Lin et al., "Synthesis and antiviral activity of various 3'-azido, 3' amino, 2',3'-unsaturated and 2',3'-dideoxy analogues of pyrimidine, deoxyribonucleosides against retroviruses", J. Med. Chem., 30, pp. 440–41 (1987).

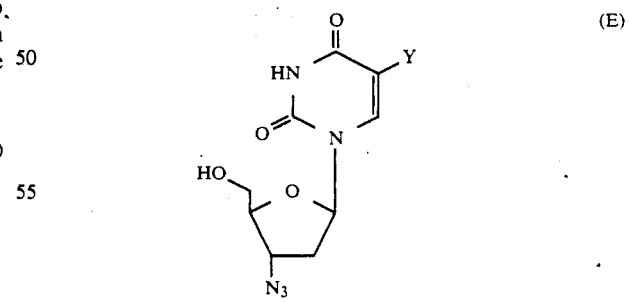

(E)

Finally, the 3'-fluoro analogues of 2',3'-dideoxycytidine shown in Formula (F) and of 2',3'-dideoxythymidine shown in Formula (G) are referred to in Herdewijn et al., "3'-Substituted 2',3'-dideoxynucleoside analogues as potential anti-HIV(HTLV-III/LAV) agents", J. Med. Chem., 30, pp. 1270–78 (1987), as having potent antiretroviral activity.

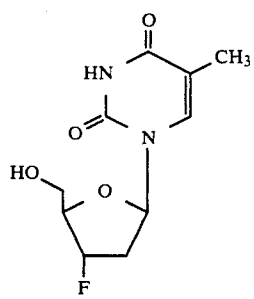

(F)

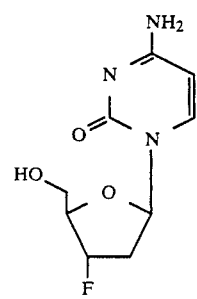

(G)

The most potent anti-HIV compounds thus far reported are 2′,3′-dideoxynucleosides, more particularly, 2′,3′-dideoxy cytidine (ddCyd) and 3′-azido-2′,3′-dideoxythymidine (AzddThd or AZT). These compounds are also active against other kinds of retroviruses such as the Moloney murine leukemia virus. Because of the increasing incidence and the life-threatening characteristics of AIDS, efforts are being expended to discover and develop new nontoxic and potent inhibitors of HIV and blockers of its infectivity. It is therefore an object of the present invention to provide effective anti-HIV compounds of low toxicity and a synthesis of such new compounds that is readily feasible.

DISCLOSURE OF INVENTION

A structurally distinct class of compounds known as 2-substituted-5-substituted-1,3-oxathiolanes has now been discovered and found to have antiretroviral activity. In particular, these compounds have been found to act as non-toxic inhibitors of the replication of HIV-1 in T-lymphocytes over prolonged periods of time. Accordingly, the present invention provides a compound of Formula (I):

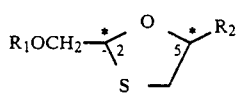

(I)

$R_1$ may be selected from the group consisting of hydrogen, an acyl group having from 1 to 16 carbon atoms, preferably, benzoyl or a benzoyl substituted in any position by at least one halogen (bromine, chlorine, fluorine, or iodine), $C_{1-6}$ alkyl, $C_{1-6}$ alkoxy, nitro or trifluoromethyl groups $R_2$ is a heterocyclic radical selected from:

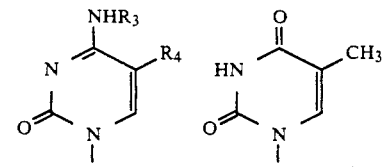

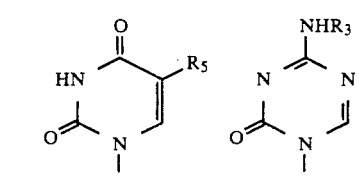

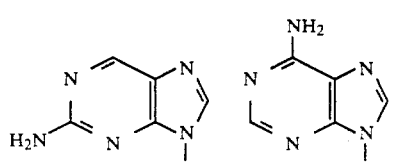

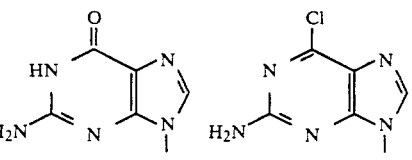

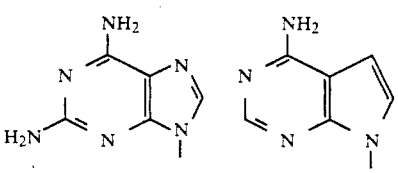

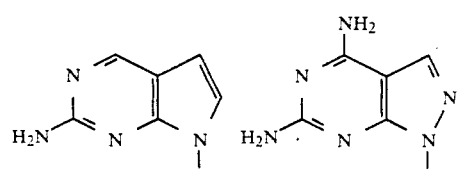

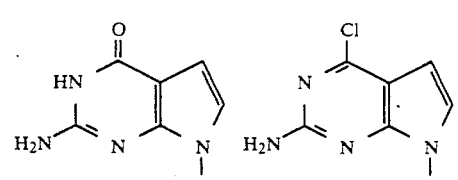

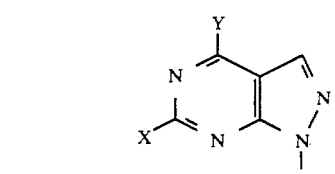

$R_3$ and $R_4$ are independently selected from the group of hydrogen or $C_{1-6}$ alkyl groups, $R_5$ is selected from the group of hydrogen, $C_{1-6}$ alkyl, bromine, chlorine, fluorine, or iodine, and X and Y are independently selected from the group of bromine, chlorine, fluorine, iodine, amino or hydroxy groups. Of particular interest are the following compounds of formula (I):

(a) $R_1$ is hydrogen and $R_2$ is cytosin-1'-yl;
(b) $R_1$ is hydrogen and $R_2$ is thymin-1'-yl;
(c) $R_1$ is hydrogen and $R_2$ is uracil-1'-yl;
(d) $R_1$ is hydrogen and $R_2$ is adenosin-9'-yl;
(e) $R_1$ is hydrogen and $R_2$ is inosin-9'-yl;
(f) $R_1$ is hydrogen and $R_2$ is 5-aza-cytosin-1'-yl;
(g) $R_1$ is hydrogen and $R_2$ is 2'-amino-purin-9'-yl;
(h) $R_1$ is hydrogen and $R_2$ is 2'-amino-6'-chloro-purin-9'-yl;
(i) $R_1$ is hydrogen and $R_2$ is 2',6'-diamino-purin-9'-yl; and
(j) $R_1$ is hydrogen and $R_2$ is guanin-9'-yl.

Also included in this invention are the oxidized forms of Formula (I) as shown in Formulas (II) and (III).

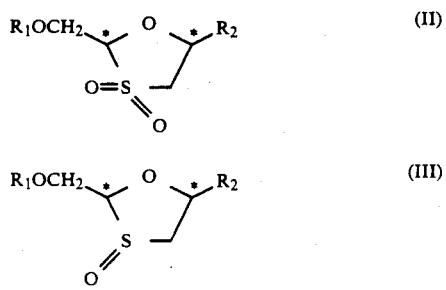

There are two asymmetric carbons noted by asterisks in the Formulas (I), (II) and (III) which lead to two racemic forms (±) and therefore, four optical isomers. These racemates differ in the relative configurations of the 2- and 5- substituents which can either assume the cis- or trans- configurations. The use of the graphic representation of Formulas (I), (II) and (III) is meant to include the dl- or racemic mixtures as well as their separate d-and l- isomers. The sulfoxide derivative of Formula (III) exists in two additional racemic forms as shown in Formulas (IIIa) and (IIIb) which differ in the configuration of the oxide oxygen atom relative to the 2,5-substituents. Accordingly, Formula (III) includes both forms as well as mixtures of them.

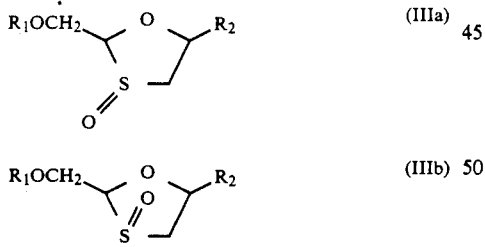

The present invention also provides a process for the preparation of compounds having Formulas (I), (II) and (III). This process, in which $R_2$ is cytosin-1'-yl is illustrated in SCHEME I. The various steps involved in the synthesis as illustrated in Scheme 1 may be briefly described as follows:

Step 1: Commercial bromoacetaldehyde diethyl acetal (or an equivalent halo alkyl acetal) is treated in boiling DMF with an excess of potassium thiobenzoate to give the benzoylthio acetal of Formula V.

Step 2: The benzoyl group of Formula V is hydrolyzed with sodium hydroxide in an aqueous organic solvent to give the known mercaptoacetal shown in Formula VI (G. Hesse and I. Jorder, "Mercaptoacetaldehyde and dioxy-1, 4-dithiane", *Chem. Ber.*, 85, pp. 924–32 (1952)).

Step 3. Glycerol 1-monobenzoate prepared according to the literature (E. G. Hallonquist and H. Hibbert, "Studies on reactions relating to carbohydrates and polysaccharides. Part XLIV: Synthesis of isomeric bicyclic acetal ethers", *Can. J. Research*, 8, pp. 129–36 (1933)), is oxidized with sodium metaperiodate to give the known benzoyloxyacetaldehyde of Formula VII (C. D. Hurd and E. M. Filiachione, "A new approach to the synthesis of aldehyde sugars", *J. Am. Chem. Soc.*, 61, pp. 1156–59 (1939)).

Step 4. The aldehyde of Formula VII is then condensed with mercaptoacetal of Formula VI in a compatible organic solvent, such as toluene, containing a catalytic amount of a strong acid to give the novel intermediate shown in Formula VIII.

Step 5. The 1,3-oxathiolane of Formula VIII is then reacted with cytosine previously silylated with hexamethyldisilazane in a compatible solvent using a Lewis acid or trimethylsilyl triflate to give intermediate of Formula IX.

Step 6. The amine function of the compound shown in Formula IX is acetylated with acetic anhydride to yield the intermediate of Formula X as cis- and trans-isomers.

Step 7: The cis- and trans- isomers of Formula X are treated with methanolic ammonia to obtain the desired product shown in Formula XI as cis- and trans- isomers.

Step 8: The preceding isomers of Formula XI are treated with an oxidizing agent which may be a suitable peracid in a compatible solvent to give the 5-oxide (sulfoxide) of Formula XII.

This synthesis is applicable to any nucleoside base analogue as would be obvious to those skilled in the art of nucleoside chemistry. Other analogues defined by Formulas (I), (II), (IIIa) and (IIIb) may be obtained similarly from intermediate VII by using the appropriate heterocyclic compound in place of cytosine in Step 5. In Step 4, other esters of hydroxyacetaldehyde such as aliphatic acyl or substituted aroyl groups can be used following the same sequence of steps eventually leading to XI and XII respectively.

A preferred embodiment of the present invention is the compounds having Formulas (I) and (III)

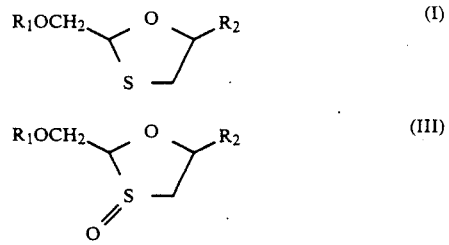

wherein $R_1$ is selected from the group comprising H, $CH_3CO-$, $CH_3(CH_2)_2CO-$, $CH_3(CH_2)_{10}CO-$, $CH_3(CH_2)_{12}CO-$, and $CH_3(CH_2)_{14}CO-$ or aroyl or substituted aroyl residues such as $C_6H_5CO-$ and its ortho, meta and para substituted derivatives comprising halogens (bromine, chlorine, fluorine or iodine), $C_{1-6}$ alkyls, methoxy, $C_{1-6}$ alkoxy, nitro, trifluoromethyl groups; and $R_2$ is selected from the group comprising cytosin-1'-yl, adenosin-9'-yl, thymin-1'-yl, guanosin-9'-yl, uracil-1'-yl, inosin -9'-yl, and analogous heterocycles such as 5-aza-cytosin-1'-yl, 5'-ethyluracil-1'-yl, N4,5'-dimethylcytosin-1'-yl, 5'-fluorouracil-1'-yl, 5'-iodouracil-1'-yl, or other related heterocycles well known to those familiar with nucleoside analogue chemistry and biochemistry.

A more preferred embodiment is the compounds of Formulas XI, XII, and XIII

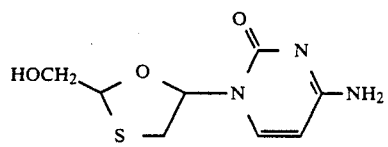
(XI)

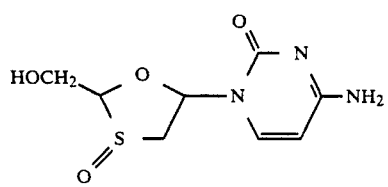
(XII)

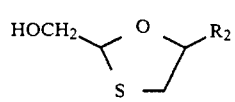
(XIII)

wherein $R_2$ comprises adenosin-9'-yl, thymin-1'-yl, inosin-9'-yl, uracil-1'-yl and 5-aza-cytosin-1'-yl and where the sulfur atom may be in the sulfoxide form.

In vitro testing was conducted on the compounds designated herein as cis-XI and trans-XI to determine their inhibitory properties. The results are shown in Tables 1 and 2. The concenrations reported are ug/ml in the incubation media which affect the susceptibility of a continuous line of T-cells developed at the Lady Davis Institute for Medical Research (Montreal) by Dr. Mark A. Wainberg toward infection by HIV-1 following a protocol similar to that of H. Mitsuya and S. Broder, "Inhibition of the in vitro infectivity and cytopathic effect of human T-lymphotropic virus type III/-lymphadenopathy-associated virus (HTLV-III/LAV) by 2'3'-dideoxynucleosides", *Proc. Natl. Acad. Sci. USA*, 83, pp. 1911–15 (1986). Protection of the cell line from infection was monitored by staining with monoclonal antibodies against viral proteins in the standard manner (Table 1). In all experiments, comparisons were made with the drug AZT as the control. In order to confirm the results, the drug effects were monitored by measuring reverse transcriptase (RT) activity in the U-937 line of human monocytic cells as assayed in the usual manner with tritiated thymidine triphosphate (TTP) (Table 2). Finally, the drug effects on cell viability as measured by the well-know cytolytic effects of HIV-1 on the MT-4 cell line was evaluated in the accepted manner (Table 1).

It is apparent from the results of Table 1 that compound cis-XI exerts potent inhibitory activity against HIV-1, surpassing the potency of AZT in some respects. In some assays, significant inhibitory activity was also observed with the trans- isomer of XI. As is usually observed with compounds of type XI, the cis-isomer especially is expected to demonstrate in vivo activity as an inhibitor of retroviruses. It may also be used in combination with other antiviral agents at reduced doses owing to the possibility of synergistic effects.

Toxicity

No toxic effects were observed in the above tests.

TABLE 1

Inhibition of HIV-1 product by cis-XI in MT-4 cells (a) Viable Counts

| Time in Culture (Days) | Cell Viability % | | |
|---|---|---|---|
| | No Drug | 2 ug/ml AZT | 2 ug/ml cis-XI |
| 3 | 86.7 | 95.0 | 94.0 |
| 6 | 6.47 | 88.6 | 87.4 |

(b) P-24 immunofluorescence

| Time in Culture (Days) | Immunofluorescent Cells | | |
|---|---|---|---|
| | No Drug | 2 ug/ml AZT | 2 ug/ml cis-XI |
| 3 | 5.9 | 1.0 | 1.0 |
| 6 | 99 | 1.0 | 7.6 |

(c) Reverse transcriptase assay

| | 6 | 339.0 | 1.748 | 2.301 |
|---|---|---|---|---|
| Time in Culture | RT Activity (CPM × 1000)/ml | | | |
| (Days) | No Drug | 2 ug/ml AZT | 2 ug/ml cis-XI | |
| 3 | 36.43 | 1.564 | 2.381 | |
| 6 | 339.0 | 1.748 | 2.301 | |

TABLE 2

Inhibition of HIV-1 production by cis-XI in H-9 cells
Reverse transcriptase assay

| Time in Culture (Days) | RT Activity (CPM × 1000)/ml | | |
|---|---|---|---|
| | No Drug | 2 ug/ml AZT | 2 ug/ml cis-XI |
| 5 | 9.117 | 3.346 | 3.077 |
| 8 | 438.5 | 3.414 | 5.853 |
| 11 | 2550 | 2.918 | 3.560 |
| 14 | 2002 | 8.320 | 2.872 |
| 17 | 584.5 | 2.997 | 2.399 |
| 21 | 365.2 | 3.111 | 2.907 |
| 25 | 436.4 | 15.88 | 4.020 |
| 29 | 92.38 | 32.08 | 3.756 |
| 33 | 111.1 | 612.2 | 3.803 |
| 37 | 32.28 | 878.2 | 4.193 |
| 41 | 384.4 | 994.0 | 4.515 |
| 45 | 33.64 | 32.91 | 3.441 |

Also in accordance with the present invention, there is provided a pharmaceutical composition for administration to persons infected with the AIDS virus or other infectious agent which comprises a therapeutically effective amount of the 2-substituted-5-substituted-1,3-oxathiolane of Formula I, II, or III. Depending upon the route of administration, which could normally be either oral or parenteral, the compounds may be in the form of a solid, semi-solid, liquid, oil, or ingestible capsule and may either be present as the original compound or in the form of a pharmaceutically acceptable salt in association with or without an appropriate pharmaceutical carrier.

Also within the scope of the present invention is a method for treating AIDS-infected persons by administering a therapeutically effective amount of 2-substituted-5-substituted-1,3-oxathiolane of Formula I, II or III or any combination of a 2-substituted-5-substituted-1,3-oxathiolane of Formula I, II or III with any other drug where such combination is therapeutically advantageous. The therapeutically antiviral effective amount of the compounds to be used in accordance with this invention to provide prophylaxis and treatment for individuals infected with, or at risk of being infected with HIV, can be determined by methods known in the art.

The following Examples illustrate the preparation of the compounds and intermediates of the invention. All temperatures are in degrees celsius.

EXAMPLES

Example 1

2-thiobenzoyl acetaldehyde diethyl acetal (V, Scheme 1)

To a solution of potassium t-butoxide (11.5 g. 0.11 mol) in DMF (100 m) was added thiobenzoic acid (17 g. 0.11 mol) and the solution partially evaporated in vacuo, benzene added in two consecutive portions ($2 \times 30$ ml) and evaporated in vacuo each time. To the residual DMF solution was added bromoacetaldehydediethy acetal (20.3 g. 0.1 mol) and the mixture stirred at 120° for 15 h. After cooling, it was poured onto water (500 ml), the product extracted with ether ($3 \times 200$ ml), the extract washed with aqueous $NaHCO_3$ followed by water, then dried and the solvent removed in vacuo. The residue was distilled in vacuo to give 17.2 g. of pure V, b.p. 131°–133°/0.07 mm. It was characterized by 'H NMR $\delta$(ppm, $CDCl_3$):

7.97 (d, 2H; aromatic);
7.47 (m, 3H; aromatic);
4.59 (t, 1H; —$CH(OC_2H_5)_2$));
3.66 (m, 4H; 2X $OCH_2CH_3$);
3.30 (d, 2H; $SCH_2$—);
1.23 (t, 6H; 2 X $OCH_2CH_3$);

Example 2

Mercaptoacetaldehyde diethylacetal (VI, Scheme 1)

The preceding thiobenzoyl derivative V (17.2 g) was dissolved in 100 ml THF followed by the addition of 6 g NaOH in 20 ml $H_2O$. The mixture was refluxed under $N_2$ for 15 h, then cooled and diluted with water (200 ml) and the product extracted with ether ($3 \times 200$ ml). The extract was dried, the solven removed in vacuo and the residue distilled in vacuo to yield 7.1 g of $\delta$(ppm, $CDCl_3$):

4.51 (t, 1H; $CH(OC_2H_5)_2$);
3.51 (m, 4H; 2 X $OCH_2CH_3$);
2.65 (dd, 2H; HS—$CH_2$);
1.54 (t, 1H; HS—).

Example 3

Benzoyloxyacetaldehyde (VIII, Scheme 1)

This known intermediate was prepared by a previously unreported method from the known 1-benzoyl glycerol. Thus, 50 g of the latter in a mixture of 500 ml of $CH_2Cl_2$ and 25 ml of $H_2O$ was treated portionwise with 80 g of $NaIO_4$ under vigorous stirring at room temperature. After addition, stirring was continued for 2 h after which time 100 g of $MgSO_4$ was added and stirring continued for 30 min. The mixture was filtered, the filtrate evaporated in vacuo and the residue distilled in vacuo to yield 26 g of pure VII b.p. 92°–94°/0.25 mm. 'H NMR (200 MHZ; $CDCl_3$, TMS as internal reference): $\delta$(ppm):

9.71 (s, 1H; —CHO);
8.11 (d, 2H; aromatic);
7.60 (m, 1H; aromatic);
7.46 (m, 2H; aromatic);
4.88 (s, 2H; —$CH_2CHO$).

Example 4

2-Benzoyloxymethyl-5-ethoxy-1,3-oxathiolane (VIII, Scheme 1)

The preceding mercaptoacetaldehyde acetal VI (7 g) was mixed in 100 ml of toluene with 7 g of the above benzoyloxyacetaldehyde VII, a few crystals of p. toluenesulfonic acid added and the mixture place in an oil-bath at 120° under $N_2$. The formed ethanol was allowed to distill over, the mixture kept at 120° for 30 min. longer than cooled and washed with aqueous $NaHCO_3$, dried and evaporated in vacuo. The residue was distilled in vacuo to yield 9.8 g of pure VII as a mixture of cis- and trans-isomers, b.p. 140°–143°/0.1 mm; $R_1$0.51 (hexane-EtOAc); $\delta$(ppm, $CDCl_3$):

---

8.05 (m, 2H; aromatic);
7.57 (m, 1H; aromatic);
7.43 (m, 2H; aromatic);

5.55 (m, 2H; $\underline{C_5}$—H, $\underline{C_2}$—H);

4.55 (m, 2H; $\underline{C_2}$—$CH_2O_2C_6H_5$);

3.80 (m, 1H; $C_5$—OCHCH$_3$);
          H 3.76 (m, 1H; $C_5$—OCHCH$_3$);
          H 3.76 (m, 1H; $\underline{C_5}$—OCHCH$_3$);
          H 3.17 (m, 2H; $C_4$—$H_2$);

1.21 (t, 3H; $\underline{C_5}$—OCH$_2$CH$_3$).

---

Example 5

Cis- and trans-2-benzoyloxymethyl-5-cytosin-1'-yl-1,3-oxathiolane (IX, Scheme 1)

A mixture of 2.7 g of cytosine, 30 ml of hexamethyldisilazane (HMDS) and 0.3 ml of trimethylsilyl chloride (TMSCl) was heated under reflux under dry $N_2$ until a clear solution resulted (3 L) and the excess reagents evaporated in vacuo. The remaining volatiles were removed under high vacuum (15 min.), the solid residue taken up in 250 ml of dichlorethane and 5 g of the above key intermediate VIII in 50 ml of dichloroethane added under dry argon followed by 4.7 ml of trimethylsilyl triflate (TMST$f$). After 3 days of heating under reflux under argon, it was cooled and poured onto 300 ml of saturated aqueous $NaHCO_3$. The organic layer was collected, the aqueous phase extracted with $CH_2Cl_2$ (2 X 100 ml) and the combined extracts washed with water, dried and evaporated in vacuo. The residue was purified by chromatography on silica gel using $CH_2Cl_2$—$CH_3OH$ 9:1 as the eluant to give 2.5 g of a pure mixture of cis- and trans-IX (Scheme 1) in a 1:1 ratio as ascertained by 'H NMR. These were separated as the N-acetyl derivatives as described in the following example.

Example 6

Cis-and trans-isomers of 2-benzoyloxymethyl-5-($N_4'$-acetyl-cytosin-1'-yl)-1,3-oxathiolane (X, Scheme 1)

The preceding mixture IX (2.5 g) in 100 ml of dry pyridine containing 0.1 g of 4-dimethylaminopyridine (DMAP) was treated with acetic anhydride (7 ml) at room temperature and after 16 h, the mixture was poured onto cold water followed by extraction with $CH_2Cl_2$ (3 X 150 ml). The extract was washed with water, dried, and evaporated in vacuo. Toluene was added to the residue, then evaporated in vacuo and the residual oil purified by chromatography on silica gel using $EtOAc-CH_3OH$ 99:1 as the eluant to yield 1.35 g of pure trans-X as the fast moving product and 1.20 g of pure cis-X as the slow moving component. These were characterized by 'H NMR spectroscopy:trans-X: m.p. 158°–160°; $R_f$ 0.48 ($EtOAc-CH_3)H$ 95:5). $\delta$(ppm, $CDCl_3$):

- 9.00 (b, 1H; $C_4'$—NH—Ac);
- 8.06 (m, 2H; aromatic);
- 7.74 (d, 1H; $C_6'$—H);
- 7.56 (m, 1H; aromatic);
- 7.47 (d, 1H; $C_5'$H);
- 7.45 (m, 2H; aromatic)
- 6.53 (dd, 1H; $C_5$—H);
- 5.89 (dd, 1H; $C_2$—H);
- 4.46 (dd, 2H; $C_2$—$CH_2OCOC_6H_5$);
- 3.66 (dd, 1H; $C_4$—H);
- 3.32 (dd, 1H; $C_4$—H);
- 2.25 (s, 3H; NH—$COCH_3$).

U.V. ($CH_3OH$)
Lambda max: 297 nm.

Cis-X: m.p. 150°–152°; $R_f$ 0.40 (EtOAc-MeOH 95:5). $\delta$(ppm, $CDCl_3$):

- 9.03 (b, 1H; NH—Ac);
- 8.21 (d, 1H; $C_6'$—H);
- 8.05 (m, 2H; aromatic);
- 7.60 (m, 1H; aromatic);
- 7.50 (m, 2H; aromatic);
- 7.29 (d, 1H; $C_5'$—H);
- 6.34 (dd, 1H; $C_5$—H);
- 5.52 (dd, 1H; $C_2$—H);
- 4.80 (dd, 2H; $C_2$—$CH_2OCOC_6H_5$);
- 3.66 (dd, 1H; $C_4$—H);
- 3.24 (dd, 1H; $C_4$—H);
- 2.23 (s, 3H; NH—$COCH_3$).

U.V.: ($CH_3OH$)
Lambda max: 297 nm.

Example 7

Cis- and trans-isomers of 2-hydroxymethyl-5-(cytosin-1'-yl)-1,3-oxathiolane (XI, Scheme 1)

a) Trans-XI: 375 mg of the preceding trans-X was dissolved in 100 ml of methanolic ammonia at 24° and after stirring for 16 h, the solvent was removed in vacuo and the residue crystallized with ether. It was recrystallized from ethanol-ether to yield 174 mg of pure product, m.p. >220° (dec). It was characterized by 'H and $^{13}C$ NMR. 'H NMR:$\delta$(ppm, DMSO-$d_6$:

- 7.57 (d, 1H; $C_6'$—H);
- 7.18 (d, 2H; $C_4'$—$NH_2$);
- 6.30 (dd, 1H; $C_5$—H);
- 5.68 (d, 1H; $C_5'$—H);
- 5.48 (t, 1H; $C_2$—H);
- 5.18 (t, 1H; $C_2$—$CH_2OH$);
- 3.45 (m, 3H; $C_2$—$CH_2OH + C_4H$);
- 3.06 (dd, 1H; $C_4$—H).

U.V.: ($CH_3OH$)
Lambda max: 270 nm.

$C^{13}$ NMR (DMSO-$d_6$, Varian XL-300); $\delta$ in ppm:

| $C_2'$ | $C_4'$ | $C_5'$ | $C_6'$ | $C_5'$ | $C_4'$ | $C_2'$ | $\underline{C}H_2OH$ |
|---|---|---|---|---|---|---|---|
| 154.71 | 165.70 | 93.47 | 140.95 | 87.77 | 36.14 | 86.80 | 64.71 | b) Cis-XI: treating 375 mg of Cis-X by the same preceding procedure led to 165 mg of pure product after recrystallization from ethanol-ether, m.p. 171°–173°. It was characterized by 'H and $^{13}C$ NMR. 'H NMR: $\delta$(ppm, DMSO-$d_6$):

- 7.80 (d, 1H; $C_6'$—H);
- 7.20 (d, 2H; $C_4'$—$NH_2$);
- 6.18 (t, 1H; $C_5$—H);
- 5.70 (d, 1H; $C_5'$—H);
- 5.14 (t, 1H; $C_2$—$CH_2OH$);
- 3.71 (m, 2H; $C_2$—$CH_2OH$);
- 3.40 (dd, 1H; $C_4$—H).
- 2.99 (dd, 1H; $C_4$—H).

U.V.: ($CH_3OH$)
Lambda max: 270 nm.

$C^{13}$ NMR (DMSO-$d_6$: $\delta$ in ppm:

| $C_2'$ | $C_4'$ | $C_5'$ | $C_6'$ | $C_5'$ | $C_4'$ | $C_2'$ | $\underline{C}H_2OH$ |
|---|---|---|---|---|---|---|---|
| 154.63 | 165.59 | 93.86 | 140.91 | 86.47 | 36.22 | 85.75 | 62.79 |

Example 8

Cis-2-hydroxymethyl-5-(cytosin-1'-yl)-3-oxo-1,3-oxathiolane (XII, Scheme 1)

The preceding cis-XI (100 mg) in 30 ml of ice-cold methanol was treated with 93 mg of m.chloroperbenzoic acid and after stirring for 15 min a white solid separated which was collected and washed with 10 ml of methanol to give 45 mg of pure sulfoxide isomer a. The methanol filtrates were evaporated in vacuo and the solid residue washed with 15 ml of ethanoether (1:1) and then with 30 ml of ether to give 50 mg of pure sulfoxide isomer b. The isomers were characterized by 'H NMR. Isomer XII a: m.p.>270° (dec); $R_f$:0.30 ($CH_2Cl_2$—MeOH 3:1). $\delta$(ppm, DMSO-$d_6$):

- 7.68 (d, 1H; $\underline{C_6'H}$);
- 7.36 (s, 2H; $\underline{C_4'}—NH_2$);
- 6.69 (dd, 1H; $\underline{C_5'H}$);
- 5.76 (d, 1H; $\underline{C_5'}—\underline{H}$);
- 5.47 (t, 1H; $\underline{C_2}—CH_2OH$);
- 4.63 (dd 1H; $\underline{C_2}—\underline{H}$);
- 3.88 (m, 1H; $C_2—CH—OH$);
    H
- 3.72 (m, 1H; $\underline{C_2}—\underline{C}H—OH$);
    H
- 3.36 (dd, 1H; $\underline{C_4}—\underline{H}$);

3.05 (dd, 1H; C$_4$—H);

U.V.: (CH$_3$OH)
Lambda max: 270 nm.
Isomer XII b: m.p.>220° (dec); R$_f$:0.32 (CH$_2$Cl$_2$—MeOH 3:1). δ(ppm, DMSO-d$_6$):
7.76 (d, 1H; C$_6'$—H);
7.28 (d, 2H; C$_4'$—NH$_2$);
6.66 (dd, 1H; C$_5$—H);
5.77 (d, 1H; C$_5'$—H);
5.45 (t, 1H; C$_2$—CH$_2$OH);
4.64 (t, 1H; C$_2$—H);
3.77 (t, 2H; C$_2$—CH$_2$OH);
3.65 (dd, 1H; C$_4$—H).
3.17 (dd, 1H; C$_4$—H).

We claim:

1. A 1,3-oxathiolane of formula (A), the geometric and optical isomers thereof, and mixtures of those isomers:

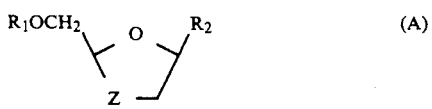

wherein:
Z is selected from the group consisting of sulfur, sulfoxide, and sulfone;
R$_1$ is selected from the group consisting of hydrogen and an acyl group having 1 to 16 carbon atoms;
R$_2$ is a heterocyclic radical selected from the group consisting of:

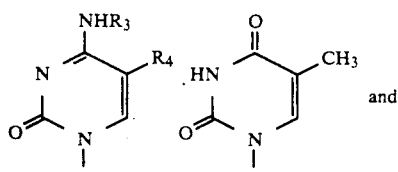

and

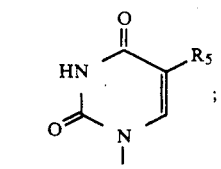

R$_3$ and R$_4$ are independently selected from the group consisting of hydrogen and C$_{1-6}$ alkyl groups;
R$_5$ is selected from the group of hydrogen, C$_{1-6}$ alkyl, bromine, chlorine, fluorine, and iodine; and
X and Y are independently selected from the group consisting of bromine, chlorine, fluorine, iodine, amino and hydroxyl groups.

2. A compound according to claim 1 wherein R$_1$ is hydrogen and R$_2$ is cytosin-1'-yl.

3. A compound according to claim 1 wherein R$_1$ is hydrogen and R$_2$ is thymin-1'-yl.

4. A compound according to claim 1 wherein R$_1$ is hydrogen and R$_2$ is uracil-1'-yl.

5. The compound according to claim 1 where R$_1$ is selected from the group consisting of acetyl, hexanoyl and benzoyl which may be substituted by a group selected from the group consisting of OH, OCH$_3$, NO$_2$, CF$_3$ and NH$_2$.

6. A method for treating human immunodeficiency virus infections in animals and humans, characterized by administering an antiviral effective amount of a compound of a 1,3-oxathiolane of Formula (A), the geometric and optical isomers thereof, and mixtures of those isomers:

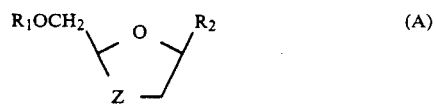

wherein:
Z is selected from the group consisting of sulfur, sulfoxide and sulfone;
R$_1$ is selected from the group consisting of hydrogen and an acyl group having 1 to 16 carbon atoms;
R$_2$ is a heterocyclic radical selected from the group consisting of:

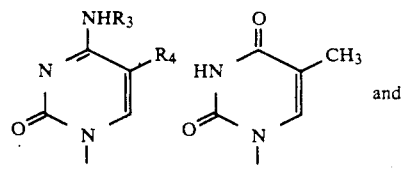

and

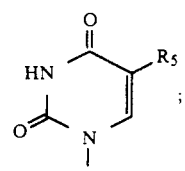

R$_3$ and R$_4$ are independently selected from the group consisting of hydrogen and C$_{1-6}$ alkyl groups;
R$_5$ is selected from the group of hydrogen, C$_{1-6}$ alkyl, bromine, chlorine, fluorine, and iodine; and
X and Y are independently selected from the group consisting of bromine, chlorine, fluorine, iodine, amino and hydroxyl groups.

7. A pharmaceutical composition for use in treating HIV infections in animals and humans, characterized by an antiviral effective amount of a compound selected from the group consisting of a 1,3-oxathiolane of formula (A), the geometric and optical isomers thereof, and mixtures of those isomers:

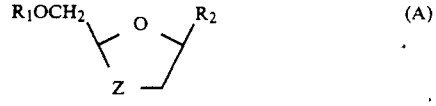

wherein:
Z is selected from the group consisting of sulfur, sulfoxide and sulfone;
R$_1$ is selected from the group consisting of hydrogen and an acyl group having 1 to 16 carbon atoms;
R$_2$ is a heterocyclic radical selected from the group consisting of:

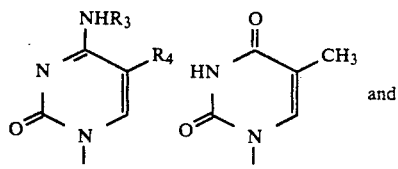
and
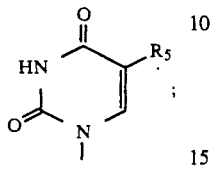
;

R₃ and R₄ are independently selected from the group consisting of hydrogen and $C_{1-6}$ alkyl groups;
R₅ is selected from the group of hydrogen, $C_{1-6}$ alkyl, bromine, chlorine, fluorine, and iodine; and
X and Y are independently selected from the group consisting of bromine, chlorine, fluorine, iodine, amino and hydroxyl groups.

8. A compound of Formula IX the geometric and optical isomers thereof, and mixtures of those isomers.

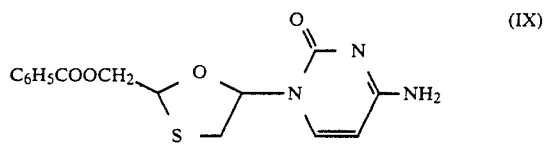 (IX)

9. A compound of Formula X the geometric and optical isomers thereof, and mixtures of those isomers.

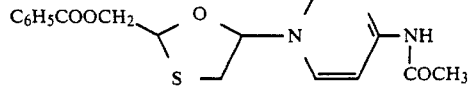 (X)

10. A compound of Formula XI the geometric and optical isomers thereof, and mixtures of those isomers.

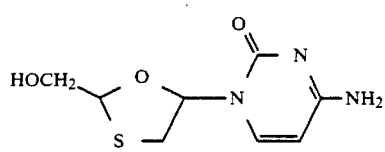 (XI)

11. A compound of Formula XII the geometric and optical isomers thereof, and mixtures of those isomers.

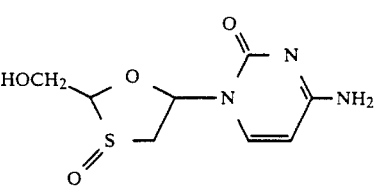 (XII)

12. The compound according to claim 1 wherein R₁ is an aroyl.
13. The compound according to claim 1 wherein R₁ is a benzoyl substituted in any position by at least one bromine, chlorine, fluorine, iodine, $C_{1-6}$ alkyl, $C_{1-6}$ alkoxy, nitro or trifluoromethyl group.

* * * * *

UNITED STATES PATENT AND TRADEMARK OFFICE
CERTIFICATE OF CORRECTION

PATENT NO. : 5,047,407
DATED : September 10, 1991
INVENTOR(S) : Bernard Belleau and Nghe Nguyen-Ba It is certified that error appears in the above-identified patent and that said Letters Patent is hereby corrected as shown below:

Col. 13, line 54, "$C_{1-6}$ alkyl groups; " should be -- $C_{1-6}$ alkyl groups; and --;

Col. 13, line 56, "and iodine; and" should be -- and iodine. --;

Col. 13, lines 57-59, delete "X and Y are independently selected from the group consisting of bromine, chlorine, fluorine, iodine, amino and hydroxyl groups.";

Col. 15, line 19, "$C_{1-6}$ alkyl groups;" should be -- $C_{1-6}$ alkyl groups; and --;

Col. 15, line 21, "and iodine; and" should be -- and iodine. --;

Col. 15, lines 22-24, delete "X and Y are independently selected from the group consisting of bromine, chlorine, fluorine, iodine, amino and hydroxyl groups.".

Signed and Sealed this

Ninth Day of March, 1993

*Attest:*

STEPHEN G. KUNIN

*Attesting Officer*   *Acting Commissioner of Patents and Trademarks*

UNITED STATES PATENT AND TRADEMARK OFFICE
CERTIFICATE OF CORRECTION

PATENT NO. : 5,047,407
DATED : September 10, 1991
INVENTOR(S) : Bernard Belleau and Nghe Nguyen-Ba It is certified that error appears in the above-identified patent and that said Letters Patent is hereby corrected as shown below:

Col. 14, line 42, "$C_{1-6}$ alkyl groups; " should be -- $C_{1-6}$ alkyl groups; and -- ;

Col. 14, line 44, "and iodine; and" should be -- and iodine. --;

Col. 14, lines 45-47, delete "X and Y are independently selected from the group consisting of bromine, chlorine, fluorine, iodine, amino and hydroxyl groups.".

Signed and Sealed this

Third Day of August, 1993

Attest:

MICHAEL K. KIRK

*Attesting Officer*   Acting Commissioner of Patents and Trademarks

UNITED STATES PATENT AND TRADEMARK OFFICE

CERTIFICATE EXTENDING PATENT TERM
UNDER 35 U.S.C. § 156

PATENT NO.      :   5,047,407

ISSUED          :   September 10, 1991

INVENTOR(S)     :   Bernard Belleau, et al.

PATENT OWNER    :   BioChem Pharma Inc.

PRODUCT         :   EPIVIR™ (lamivudine)

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

282 days from February 8, 2009, the original expiration date of the patent, subject to the provisions of 35 U.S.C. § 41(b), with all rights pertaining thereto as provided by 35 U.S.C. § 156(b).

I have caused the seal of the Patent and Trademark Office to be affixed this 16th day of April 1999.

Q. Todd Dickinson
Acting Assistant Secretary of Commerce and
Acting Commissioner of Patents and
Trademarks